Jan. 28, 1969 M. L. MEILLAND Plant Pat. 2,859
ROSE PLANT
Filed July 7, 1967
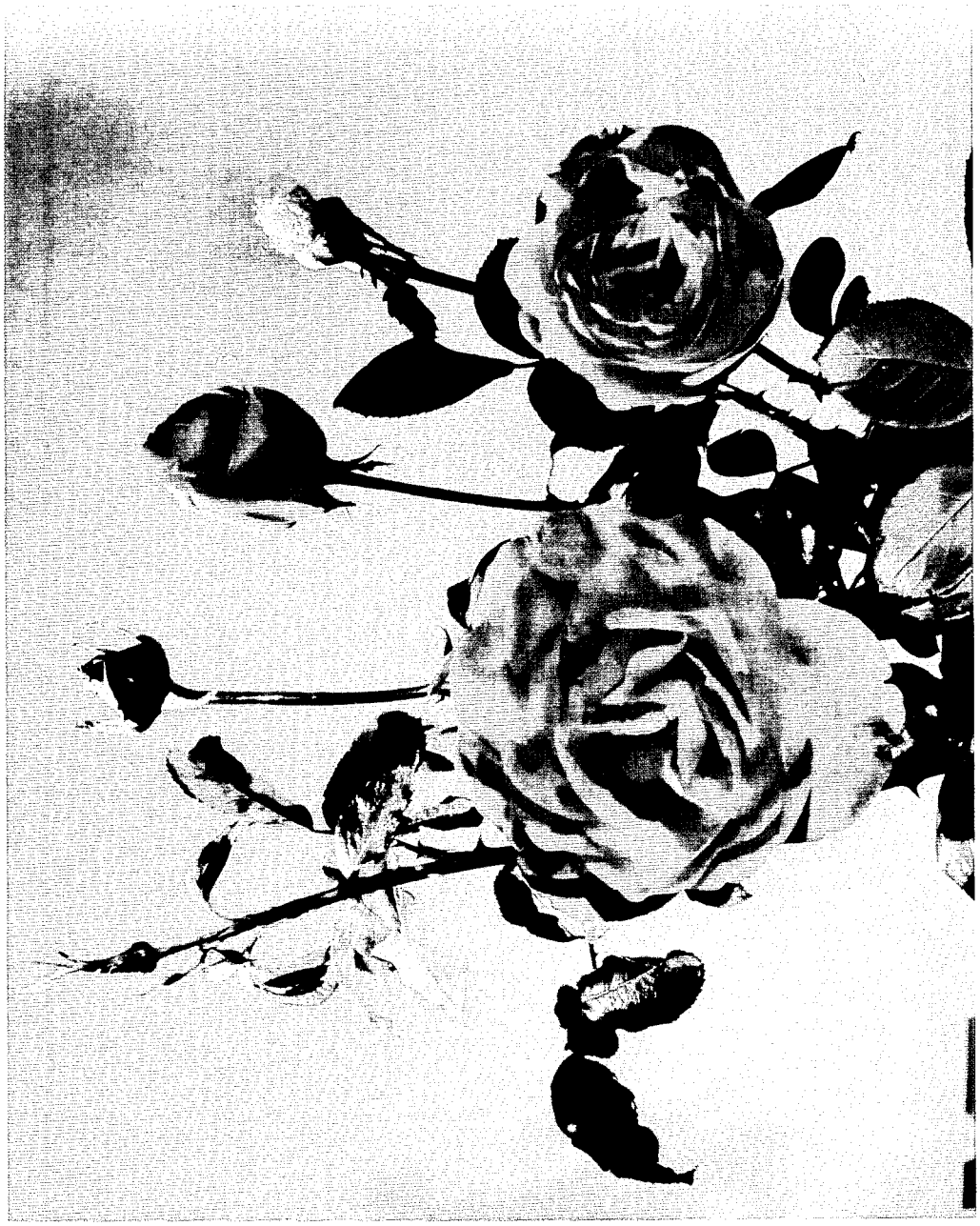
Inventor.
Marie Louise Meilland
By: Robb & Robb
Attorneys.

United States Patent Office

Plant Pat. 2,859
Patented Jan. 28, 1969

2,859
ROSE PLANT
Marie Louise Meilland, Cap-d'Antibes, Alpes-Maritimes, France
Filed July 7, 1967, Ser. No. 651,960
Claims priority, application France, July 29, 1966, 47,596
1 Claim. (Cl. Plt.—20)

The present invention relates to a new and distinct variety of rose plant of the hybrid tea class, which was originated by me by crossing the rose variety "Happiness" (U.S. Plant Patent No. 911), known in France as "Rouge Meilland," with the variety "Suspense" (U.S. Plant Patent No. 1, 944), the former being the seed parent, and the latter being the pollen parent.

As the result of this breeding, I have produced a new and improved rose variety which is distinguished from its parents, as well as from all other varieties of which I am aware, as evidenced by the following unique combination of characteristics which are outstanding therein:

(1) A vigorous, hardy, bushy, upright and well-branched habit of growth;

(2) Abundant, large, heavy foliage of an attractive Spinach Green color, having average disease resistance;

(3) A free blooming habit, with the flowers usually borne singly on long, strong stems;

(4) Firm flower petals, with attendant long lasting qualities and a habit of dropping the petals cleanly at the end of the flower life;

(5) A double flower form;

(6) A distinctive, attractive and brilliant Rose Red flower color which is retained until the petals drop; and (7) A light but penetrating centifolia flower fragrance.

Asexual reproduction of the new variety by budding, as performed in France and also at West Grove, Pa., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.
Class: Hybrid tea.
Breeding: Seedling.
*Seed parent.*—"Happiness."
*Pollen parent.*—"Suspense."
Propagation: Holds its distinguishing characteristics through succeeding propagations by budding.

*Flower*

Locality where grown and observed: West Grove, Pa., U.S.A.
Flowers Borne: Singly; on strong, long stems.
Quantity of bloom: Free, outdoors.
Continuity: Continuous.
Fragrance: Light, but penetrating. Nature—centifolia.
Bud:
*Peduncle.*—Long; medium caliper; erect; stiff; medium roughness; with medium number of green, glandular tipped hairs. Color—medium dark green.
*Before calyx breaks.*—Size—large. Form—long; pointed; with a conspicuous neck; with foliaceous appendages on the surface of the bud; with slender, medium cut foliaceous parts extending beyond the tip of the bud equal to ½ or more of its length.
*As calyx breaks.*—Color—Oxblood Red, Plate 00823.
*As first petal opens.*—Size—large. Form—long. Color: outside—Cardinal Red, Plate 822/3; inside—Current Red, Plate 821, overlaid with Chrysanthemum Crimson, Plate 824.
*Opening.*—Opens up well.
Bloom:
*Size (when fully open).*—Large; from 3½ inches to 4½ inches.
*Petalage.*—Very double; from 35 to 45 petals; arranged regularly.
*Form.*—Full at first, but becoming cupped; petals being at first loosely rolled outward, but later becoming rolled outward at maturity.
Petals:
*Texture.*—Thick.
*Appearance.*—Inside—velvety. Outside—satiny.
*Shape.*—Outer—obovate, with 1 notch. Intermediate—round, with 1 notch. Inner—obovate, with no notches.

This description of a newly opened flower was made from a rose grown outdoors during the month of September at West Grove, Pa., U.S.A.:

*Color.*—Outer petal: outside surface—Rose Madder, Plate 23, sometimes suffused with Currant Red, Plate 821/3; inside surface—Rose Red, Plate 724, overlaid with Chrysanthemum Crimson, Plate 824/1. Intermediate petal: outside surface—Rose Red, Plate 724/3; inside surface—Rose Red, Plate 724/2, deepening to Rose Red, Plate 724 at petal edge. Inner petal: outside surface—Rose Red, Plate 725/1; inside surface—near Cherry, Plate 722.

This description was made from a rose that was open for three days outdoors during the month of September at West Grove, Pa., U.S.A.:

*Color.*—Outer petal: outside surface—Tyrian Rose, Plate 24; inside surface—Cherry, Plate 722/2, over laid with Chrysanthemum Crimson, Plate 824/1. Inner petal; outside surface—Cherry, Plate 722/2; inside surface—Rose Red, Plate 724, overlaid with Chrysanthemum Crimson, Plate 824/1.
*General color effect.*—Newly opened flower—Rose Red, Plate 724. Three days open—Rose Madder, Plate 23.
*Behavior.*—Drop off cleanly.
*Flower longevity.*—On bush in garden—five days in September. Cut roses grown outdoors and kept at living-room temperatures—five days in September.

*Reproductive organs*

Stamens: Many; arranged regularly about pistils.
Filaments: Many; most with anthers; long. Color—pale pink-white.
Anthers: All open at once; medium size; seldom an anther fused with a petaloid. Color—dark brown.
Pollen: Moderate quantity. Color—gold.
Pistils: Many.
Styles: Uneven; thin; bunched.
Stigma: Color—yellow, tipped with red.
Ovaries: All enclosed in receptacle.
Hips: None observed.
Sepals: Permanent; medium length; spear-shaped; recurved.
Seeds: None observed.

*Plant*

Foliage:

*Leaves.*—Compound of 5 leaflets; abundant; large; heavy.

*Leaflets.*—Shape—ovoid, with apex acute. Base—obtuse. Margin—doubly serrate.

*Color.*—Mature: upper surface—Parsley Green, Plate 00962, with maroon at leaf margins; under surface—Lavender Green, Plate 000761. Young: upper surface—Spinach Green, Plate 0960/2, with maroon at veins and leaf margins; under surface—Willow Green, Plate 000862/1, with maroon at leaf margins.

*Rachis (the supporting stem of the compound leaf).*—Heavy, Upper side—grooved; hairy. Under side—sparsely prickly.

*Stipules.*—Moderately long; medium width; with moderately long points turning out at an angle of less than 45°; with glandular tipped hairs.

*Disease resistance.*—Comparable to that of the average variety grown under the same cultural conditions at West Grove, Pa., U.S.A.

Growth:

*Habit.*—Bushy; upright: much-branched.

*Growth.*—Free.

*Canes.*—Medium caliper.

*Main stems.*—Dull. Color—Spinach Green, Plate 0960/3. Prickles—several; color—Lettuce Green, Plate 861/3, with light red toning. Hairs—several; Color—white, with red glandular tips.

*Branches.*—Dull. Color—Scheele's Green, Plate 860/3, with occasional maroon tones. Prickles—several; color—Lettuce Green, Plate 861/3, with light red toning. Hairs—several; color—white, with red glandular tips.

*New shoots.*—Dull. Color—near Scheele's Green, Plate 060/3. Prickles—several; color Scheele's Green, Plate 060/3. Hairs—many; color—white, with red glandular tips.

I claim:

1. A new and distinct variety of rose plant of the hybrid tea class, substantially as herein shown and described, characterized particularly as to novelty by the unique combination of a vigorous, hardy, bushy, upright and well-branched habit of growth, abundant, large, heavy foliage of an attractive Spinach Green color, having average disease resistance, a free blooming habit, with the flowers usually borne singly on long, strong stems firm flower petals, with attendant long lasting qualities and a habit of dropping the petals cleanly at the end of the flower life, a double flower form, a distinctive, attractive and brilliant Rose Red flower color which is retained until the petals drop, and a light but penetrating centifolia flower fragrance.

No references cited.

ROBERT E. BAGWILL, *Primary Examiner.*